United States Patent [19]

Gevins et al.

[11] Patent Number: 5,038,782
[45] Date of Patent: * Aug. 13, 1991

[54] ELECTRODE SYSTEM FOR BRAIN WAVE DETECTION

[75] Inventors: Alan S. Gevins, San Francisco; Donald Durousseau, Oakland; Joel Libove, Fremont, all of Calif.

[73] Assignee: Sam Technology, Inc., San Francisco, Calif.

[*] Notice: The portion of the term of this patent subsequent to Oct. 30, 2007 has been disclaimed.

[21] Appl. No.: 555,305

[22] Filed: Jul. 19, 1990

Related U.S. Application Data

[63] Continuation-in-part of Ser. No. 398,758, Aug. 25, 1989, Pat. No. 4,967,038, which is a continuation-in-part of Ser. No. 287,138, Dec. 21, 1988, abandoned, which is a continuation-in-part of Ser. No. 177,681, Apr. 5, 1988, abandoned, which is a continuation-in-part of Ser. No. 942,204, Dec. 16, 1986, Pat. No. 4,736,751.

[51] Int. Cl.$^5$ .............................................. A61B 5/04
[52] U.S. Cl. ..................................... 128/644; 128/731
[58] Field of Search ............... 128/639, 644, 731, 732, 128/783, 791, 802

[56] References Cited

U.S. PATENT DOCUMENTS

| | | | |
|---|---|---|---|
| 3,411,495 | 11/1968 | Casby | 128/644 |
| 3,490,439 | 1/1970 | Rolston | 128/644 |
| 3,508,541 | 4/1970 | Westbrook et al. | 128/644 |
| 4,537,198 | 8/1985 | Corbett | 128/644 |
| 4,683,892 | 8/1987 | Johansson et al. | 128/644 |
| 4,709,702 | 12/1987 | Sherwin | 128/731 |
| 4,736,751 | 4/1988 | Gevins et al. | 128/731 |

Primary Examiner—Lee S. Cohen
Assistant Examiner—J. P. Lacyk
Attorney, Agent, or Firm—Eliot S. Gerber

[57] ABSTRACT

In a brain wave detecting system, in one embodiment, a flexible hat is placed on the head of the patient. The hat contains a plurality of electrodes conforming to the hat. A circuit board having a low-noise integrated circuit amplifier may be mounted thereon. Each electrode uses a plurality of metal conductive fingers which protrude through the hair to the scalp and provide multi-contact sites on the scalp for each electrode. The tips of each electrode contact the user's scalp to provide a redundancy of contacts for each electrode.

12 Claims, 12 Drawing Sheets

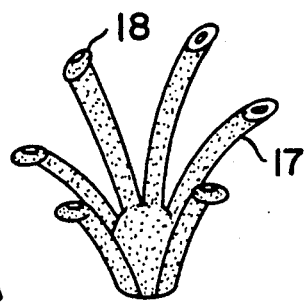
FIG. 3A
FIG. 3B
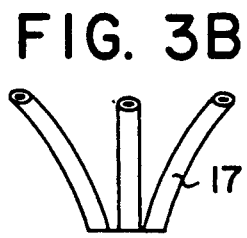
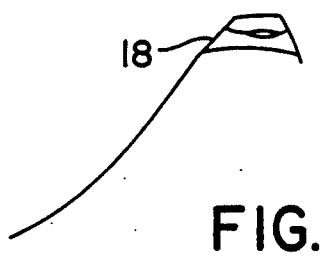
FIG. 3C
FIG. 3D
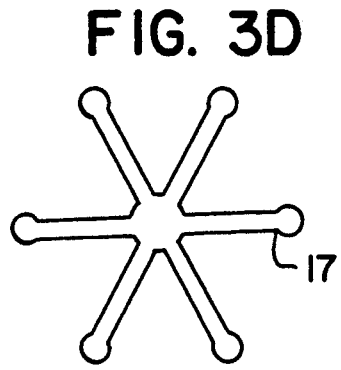
FIG. 3E
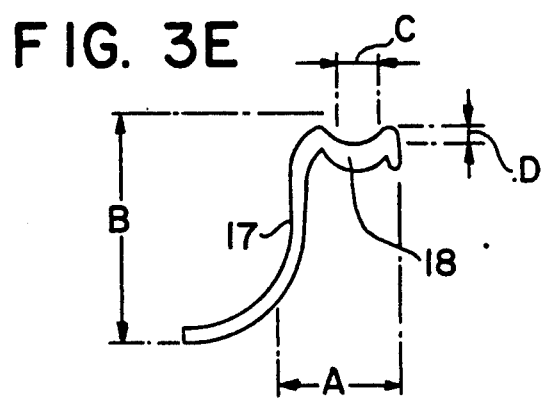

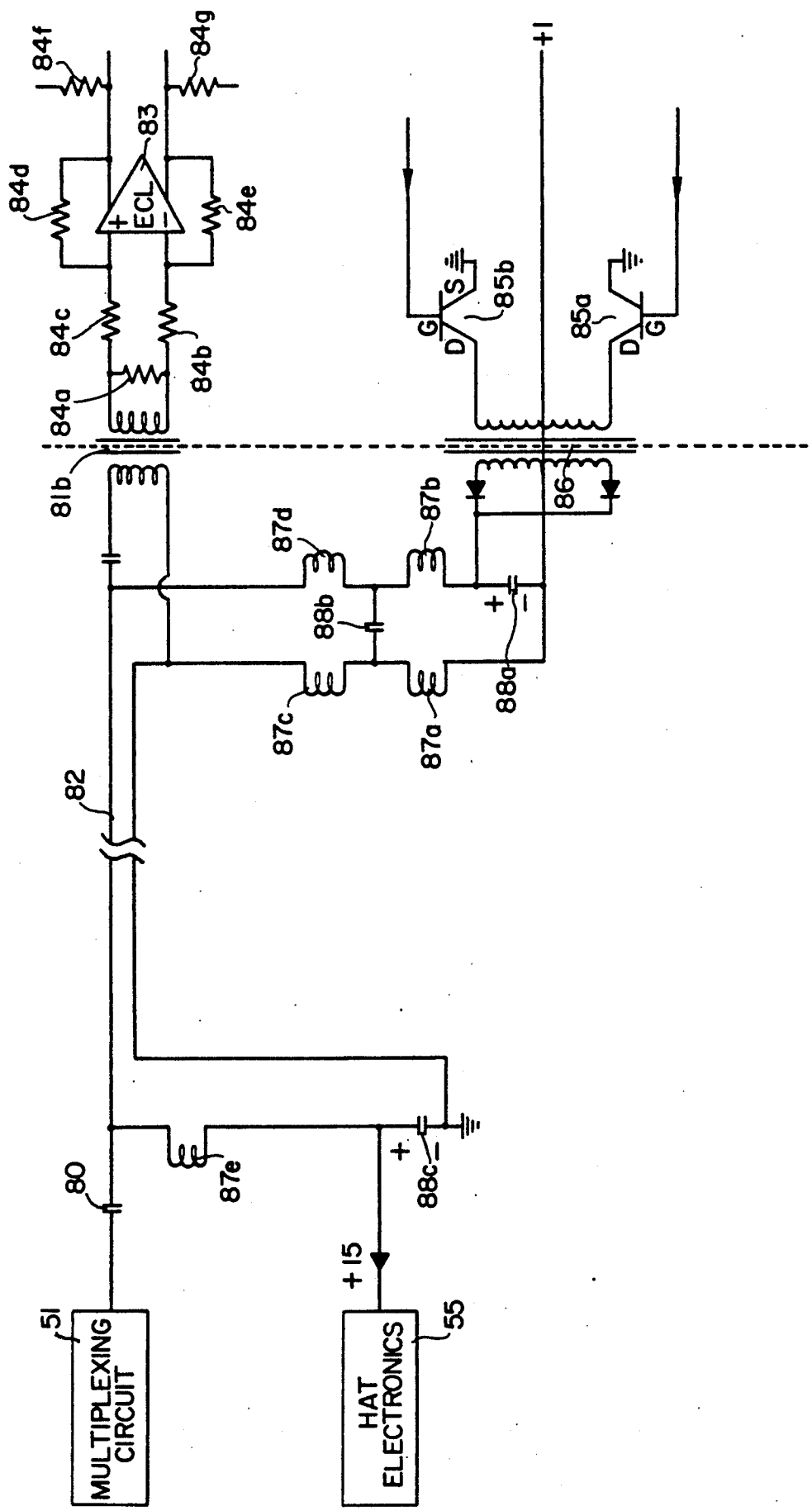
FIG. IOB

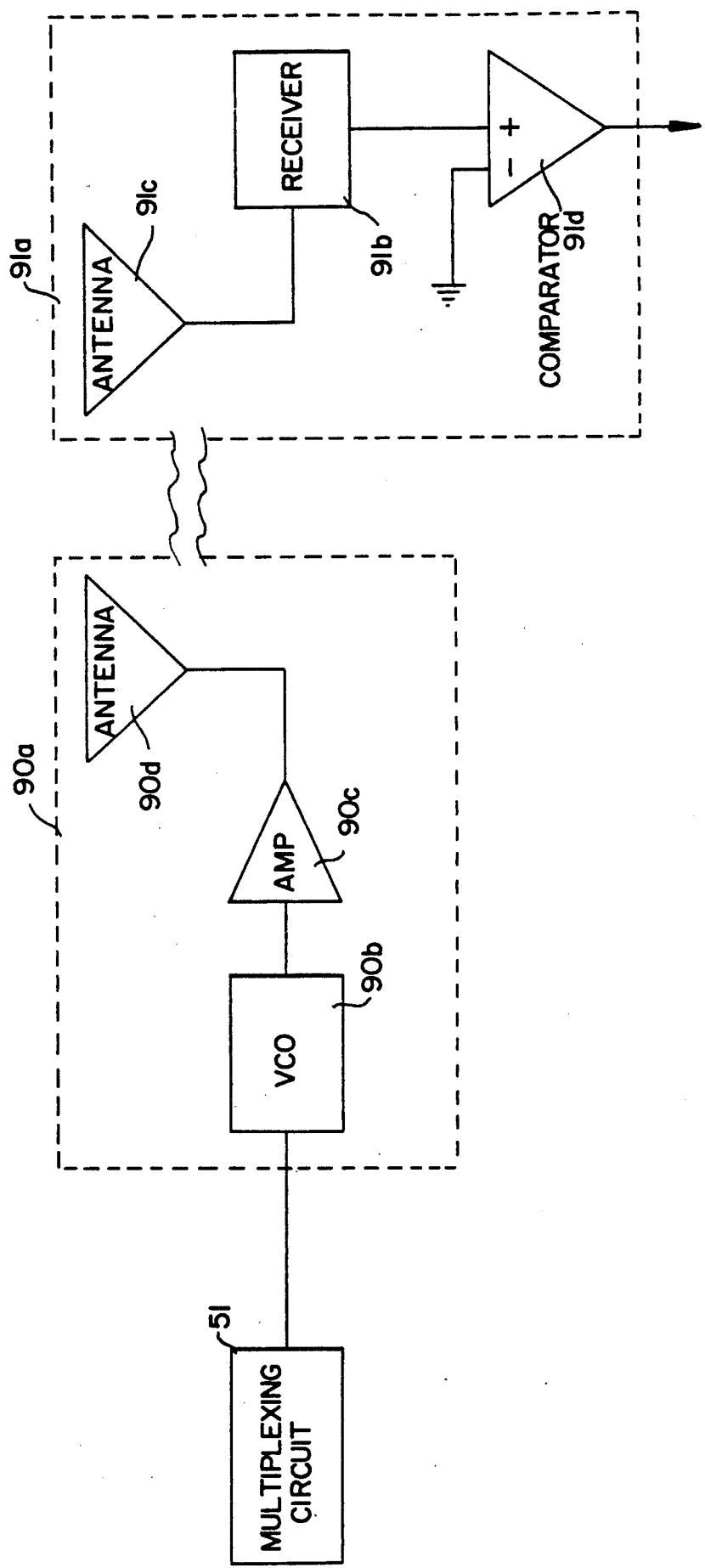

ELECTRODE SYSTEM FOR BRAIN WAVE DETECTION

This invention was made with Government Support under AFOSR Contract F33615-89-C-0605 awarded by the United States Air Force School of Aerospace Medecine, and Grant Number R44MH42725 awarded by the Alcohol, Drug Abuse and Mental Health Administration. The Government has certain rights in this invention.

BACKGROUND OF THE INVENTION

This application is a continuation-in-part application based in part on application Ser. No. 07/398,758, filed Aug. 25, 1989 and entitled "Dry Electrode Brain Recording System", now U.S. Pat. No. 4,967,038, issued Oct. 30, 1990 and entitled "Dry Electrode Brain Wave Recording System"; which was a continuation-in-part application based in part on application Ser. No. 287,138, filed Dec. 21, 1988, now abandoned, which was a continuation-in-part based in part on application Ser. No. 177,681, filed Apr. 5, 1988, now abandoned, which was a continuation-in-part based in part on application Ser. No. 942,204 for "Brain Wave Source Network Location Scanning Method and System", filed Dec. 16, 1986, now U.S. Pat. No. 4,736,751, issued Apr. 12, 1988.

FIELD OF THE INVENTION

The present invention relates to medical devices and more particularly to an improved brain wave detection scalp electrode system.

DESCRIPTION OF THE RELATED ART

Conventional techniques for recording brain waves (electroencephalograms or EEGs) of a human subject require attaching electrodes to the scalp with a low impedance connection. This involves cleaning and abrading the scalp and applying a conducting gel or solution which makes the electrical contact between the scalp and the electrode. When performed manually, the procedure takes about 20 minutes for the 19 electrodes usually used in clinical EEG examinations. Computerized EEG systems are tending towards a larger number of channels in order to better sample the brain spatially, but are limited by the increased time and effort required to apply the electrodes. For example, the most advanced research EEG systems employ 124 electrodes which takes a team of technicians more than an hour to apply.

A prior attempt to automate EEG electrode application, by Johansson, Eralp and Itil (U.S. Pat. No. 4,683,892) is based on an electromechanical design which mechanized the manual scalp preparation procedure resulting in a complex, large and heavy apparatus. This device, which looks like a hair dryer with 16 cylindrical protuberances, uses air pressure to push the electrodes into contact with the scalp and pumps which dispense an electrode gel. The device, due to its bulk, weight and mechanical complexity, is not suitable for many applications such as ambulatory monitoring, sleep studies, flight simulators, cockpits or field use.

In U.S. Pat. No. 4,709,702 to Sherwin, the electrodes contact the scalp with "tulip probes" having sharp points to "penetrate the dead skin layer". Such a sharp pointed tip is medically dangerous due to the dangers of infection and hurting the patient.

OBJECTIVES AND FEATURES OF THE INVENTION

It is an objective of the present invention to detect the brain waves of a patient at his scalp by the use of dry or semi-dry electrodes which touch the scalp and without, or with minimal use of conductive gels.

It is a further objective of the present invention that a single electrode, or a large set of such electrodes (for example, 64) may be located on the patient's scalp rapidly, with little or no preparation of the scalp.

It is a still further objective of the present invention that the placement and removal of the electrodes on the scalp should be painless and that the electrode should not abrade the skin or puncture the skin.

It is a still further objective of the present invention that the signal amplification be located close to the detecting electrodes to prevent distortion or loss of brain wave signals.

It is still a further objective of the present invention that a single electrode, or group of electrodes, may also be used to measure eye movements, muscle activity, or heart activity, by placing the electrodes in proximity with the eyes, a scalp, facial or limb muscle, or the chest, respectively.

It is a feature of the present invention to provide an electrode hat to detect brain waves from the scalp of a human subject in an electroencephalogram (EEG) system. One embodiment is a stretchable and elastic fabric hat which is adapted to stretch and fit snugly on the head of a patient. A flexible circuit board means is in contact with the hat and conducts the brain wave signals. A plurality of electrodes is mounted on the hat by, for example, snaps. Each electrode is comprised of a plurality of conductive flexible metal alloy fingers each having a dimpled free end portion. The flexible electrodes are stamped from a flat sheet, formed, heat treated and gold-plated. The dimpled free end tip is positioned at the end of each finger free end portion. The dimple allows sweat to accumulate, thus decreasing the impedance of the electrical contact at the scalp interface. Conductive means (a gold pin) conducts brain wave signals from the electrode to the circuit board means. Amplifier means, mounted on the circuit board means, amplify the brain wave signals.

Further features of the present invention are that the fabric hat consists of pieces of fabric which are sewn together to form a snugly conforming hat; a single electrode may be used or a plurality of electrodes and the flexible fingers of each electrode are at least two fingers.

In other embodiments the hat is a helmet, such as an airplane pilot's flight helmet. The electrodes may have a plurality, for example, three, flexible fingers made of conductive material. Each electrode may be held in place by a plastic holder which threads into the helmet liner. Alternatively, the electrodes may be made of a soft foam pad and covered with a conductive silver cloth which carries the signal by use of a conductive means to the printed circuit board means.

In still other embodiments, the hat is a stretchable band, such as a head band, that can hold one or more electrodes in place. In the instance in which muscle or heart activity is measured, the stretchable band can be placed around appropriate parts of the body.

In still other embodiments, the electrodes are attached to the frames of eye glasses or goggles to measure eye movement activity.

SUMMARY OF THE INVENTION

In accordance with the present invention, there is provided a method and apparatus, called a "Smart Hat", to detect a patient's brain waves with or without the use of conducting gels or pastes, and with little or no preparation of the scalp. The "Smart Hat" avoids the problems of electromechanical devices by using novel electrically buffered, multicontact electrodes which require little or no conducting gels or pastes, and which require little or no preparation of the scalp. In one embodiment, the system consists of from 1-256 multicontact electrodes mounted to the inner surface of a stretchable fabric hat. Each multicontact electrode has at least two flexible fingers. Each of 4 electrodes plugs into a Field Effect Transistor (FET) input preamplifier circuit mounted on a flexible printed circuit (PC) board. The PC board is attached to the hat with Velcro. The flexible metal fingers of the electrodes poke through the hair and the dimpled tips contact the scalp. The flexibility of the metal alloy allows the electrode to adapt to the local contour of the head. The redundancy of the multiple contacts on each electrode improves the electrical connection since it is not dependent on the impedance at a single small point. The dimpled tips of each flexible finger free end provide a recess which allows sweat to accumulate in order to decrease the impedance at the scalp interface. The hat is made from a stretchable fabric which has been cut and sewn to conform to the shape of the head. When the hat is placed on the head, the elastic fabric pushes the electrodes against the head, in turn causing the flexible metal fingers to part the hair and make contact with the scalp. The elasticity of the fabric allows a single hat to fit a variety of head shapes and sizes.

An analog embodiment of the Smart Hat records and amplifies EEGs with multicontact active electrodes and then carries the analog signals off the head with a standard cable to the input of a commercial clinical EEG amplifier system. A digital version of the Smart Hat further amplifies, filters and digitizes the brain signals and translates them to an optical form for transmission to a decoding circuit located on a parallel interface card of a computer.

In an alternate embodiment of the analog version, the amplied EEG signals are fed into an EEG analysis circuit mounted on the hat.

In an alternate embodiment of the digital version, the fiber optic communication media may be replaced with a coaxial cable for transmission to a decoding circuit located on a parallel interface card of a computer.

In an alternate embodiment of the digital version, the fiber optic communication media may be replaced with a radio frequency (RF) link for transmission to a decoding circuit located on a parallel interface card of a computer.

In an alternate embodiment of the digital version, the fiber optic communication media may be replaced with an infra-red (IR) link for transmission to a decoding circuit located on a parallel interface card of a computer.

The Smart Hat has high noise immunity and is very simple to apply. It yields signals whose quality is comparable with those recorded with conventional wet cup (gel) EEG electrodes and amplification electronics. In the preferred digital embodiment, individual analog-to-digital (A/D) converters for each channel and electrical isolation of the entire hat provide the highest possible signal fidelity.

The Smart Hat is applicable to clinical and research situations for monitoring the electrical activity of the brain.

BRIEF DESCRIPTION OF THE DRAWINGS

The following detailed description should be taken in conjunction with the accompanying drawings, in which:

FIG. 3A is a perspective picture of the multicontact dry EEG electrode of the present invention;

FIG. 3B is a side view of the embodiment of FIG. 3A;

FIG. 3C is an enlarged side plan view of an electrode free end of the embodiment of FIG. 3A;

FIG. 3D is a top plan view of the electrode of the embodiment of FIG. 3A as a flat sheet prior to being formed into an electrode;

FIG. 3E is a side plan view of an electrode free end of the embodiment of FIG. 3A;

FIG. 10B is a alternative embodiment of the coaxial cable transmission link which supplies isolated power from a computer while simultaneously transferring EEG data from the hat.

FIG. 11 is a preferred embodiment of a radio frequency (RF) transmission link;

DETAILED DESCRIPTION OF THE INVENTION

Figure 1:
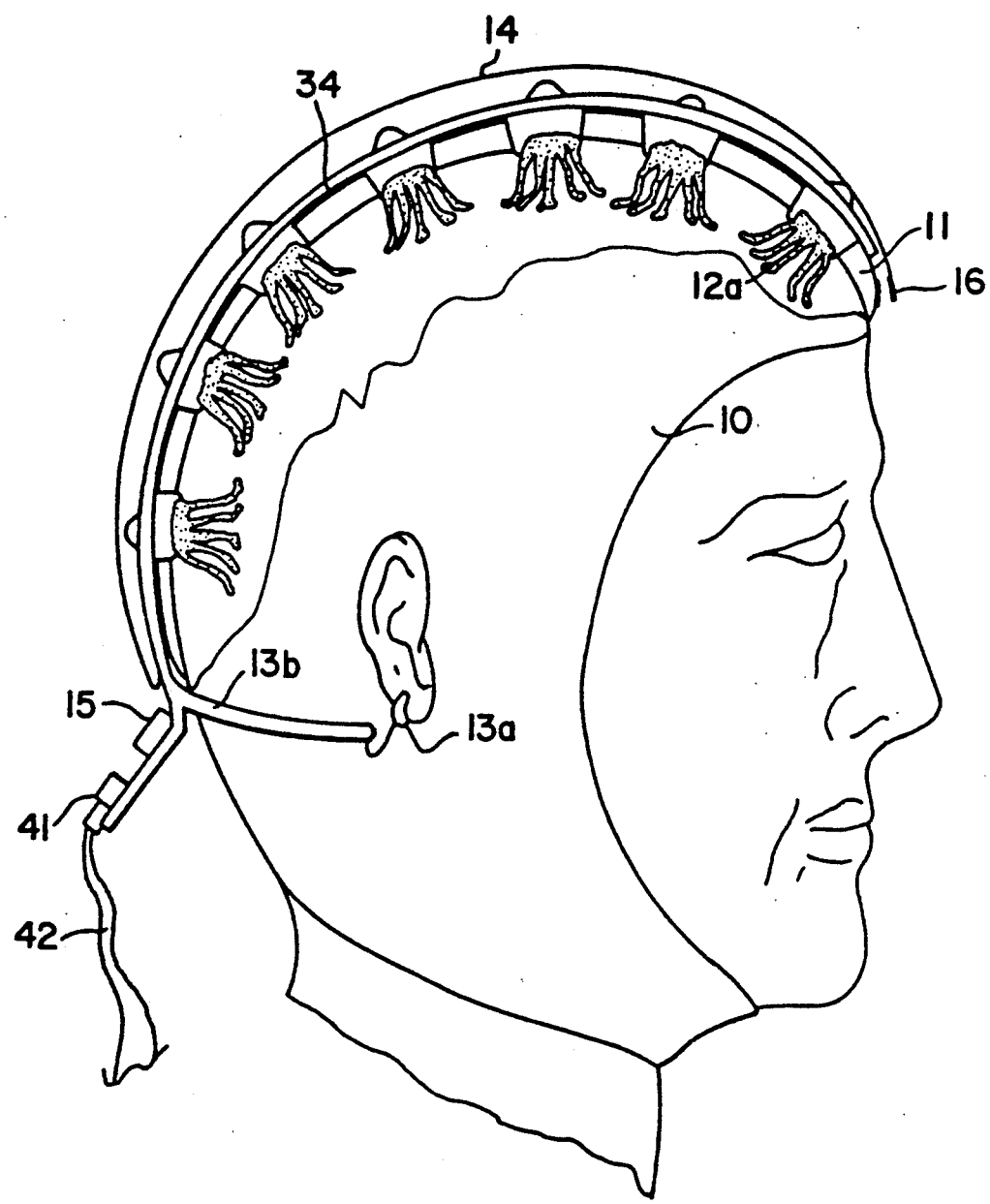
FIG. 1 is a side view in which the EEG hat of the present invention is shown in cutaway side plan, FIG. 1 being the analog embodiment of the hat.

In use, an active electrode (EEG) Smart Hat is placed on the head of the patient to detect the patient's brain waves. As shown in FIG. 1, preferably the hat 10 includes a stretchable cloth hat body 11 having 1 to 256 metal alloy, multicontact electrodes 12a-n. The designation "n" means that the number depends on the number of electrodes (channels) desired, for example, n may be in the range from 1 to 256. The hat body 11 is made from a stretch (elastic) fabric which is 69% cotton and 31% Spandex (TM).

Figure 2:
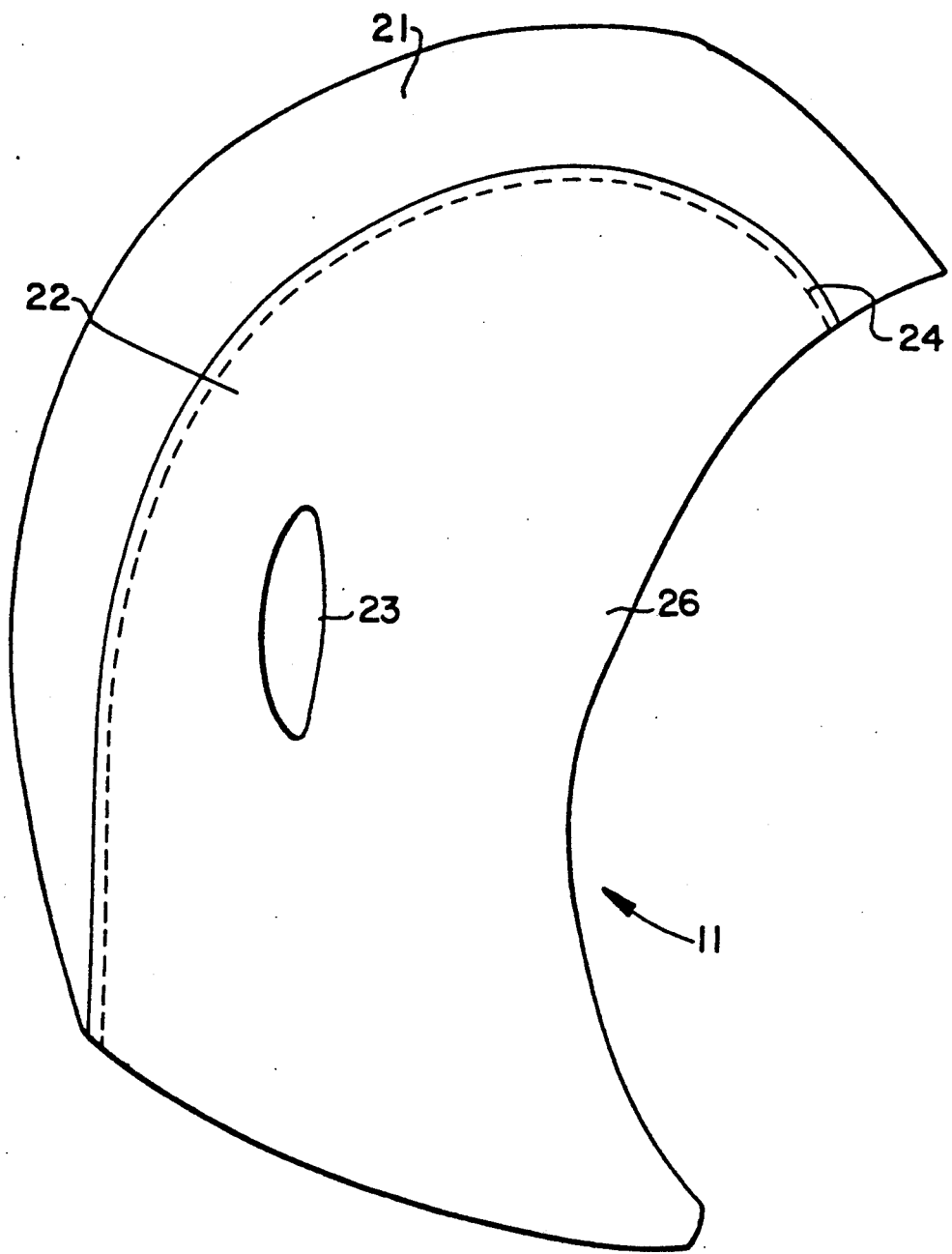
FIG. 2 is a side plan view of the construction of the stretch fabric body of the hat of FIG. 1.

As shown in FIG. 2, the fabric hat body 11 is preferably constructed out of 3 pieces of fabric. The top piece 21 extends from the front of the head to the rear of the head and is shaped to conform to the head's curvature. The two side pieces 22 are attached to the top piece 21 by cotton thread and are sewn together (indicated by dashed line 24, FIG. 2). Each side piece 22 may have a hole cut for the ear. The side pieces 22 fasten together underneath the chin. The top piece 21 covers the center of the head and is sewn to both side pieces. The stretchable fabric conforms to heads of different sizes and shapes. The hat body 11 is held down on the head by the extensions to the side pieces which fasten together under the chin. To keep hair preparation products from interfering with the contact between electrode and scalp, the subject's hair should be clean and briefly brushed with a stiff plastic bristle brush prior to putting on the hat. When the hat is placed on the head, the elastic fabric pushes the electrodes against the head, in turn causing the flexible metal fingers to part the hair and make contact with the scalp.

As shown in FIGS. 3A-3E and 4, each of the electrodes is formed from a flexible metal alloy into a shape with multiple flexible metal fingers 17 spanning from 0.5 to 4.0 cm diameter and each dimpled at the free end 18 providing a recess for sweat to accumulate. A finger 17, for example, is ⅜-inch long (dimension B), the width of the dimple 18 is 1/16-inch (dimension D), at its center, and the width of the extending portion is ⅛-inch (dimension A). The electrodes 12a-n consist of ½ hard Beryllium Copper alloy which is stamped, shaped, heat treated and gold plated. At the upper end, the electrode is soldered 20 to a gold-plated pin 30 which plugs into a connector 32 on the flexible printed circuit board 34. Each electrode is attached to the fabric hat by means of a plastic holder 26 that is sewn to the inner aspect of the fabric 11. Each electrode is attached to the holder by an enlarged area on the lower portion of the printed circuit board connector pin. The enlarged area of the connector pin fits snugly into a drilled orifice located in the center of the electrode holder 26. The flexibility of the metal alloy allows the multiple fingers to adapt to the local contour of the head. The redundancy of multiple fingers 17 improves the electrical connection since it is not dependent on the impedance at a single small point. The dimpled tips 18 at the flexible finger 17 free ends, provide a recess which allows sweat to accumulate in order to decrease the impedance at the scalp interface.

Figure 4:
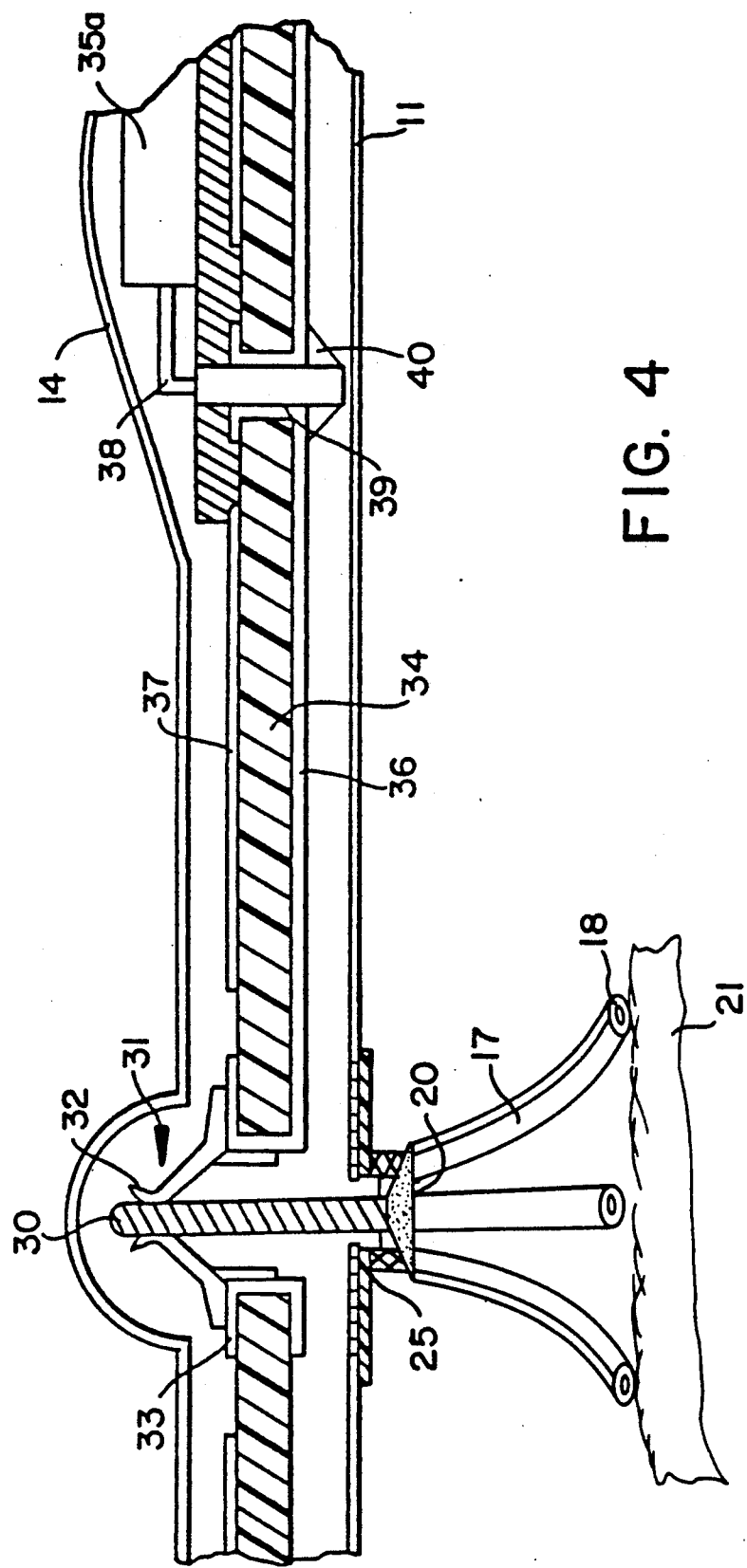
FIG. 4 is an expanded cutaway side view of the hat showing the electrodes, preamplifiers and the flexible printed circuit board.
Figure 5A:
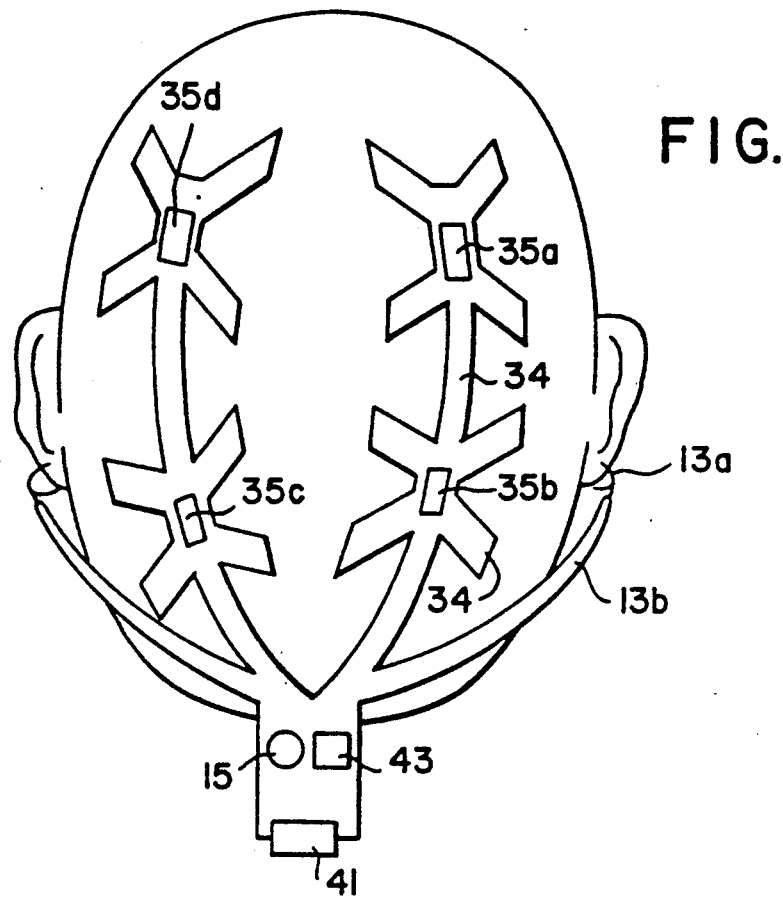
FIG. 5A is a top view of the hat with cover removed to show the flexible printed circuit boards and preamplifier circuits.
Figure 5B:
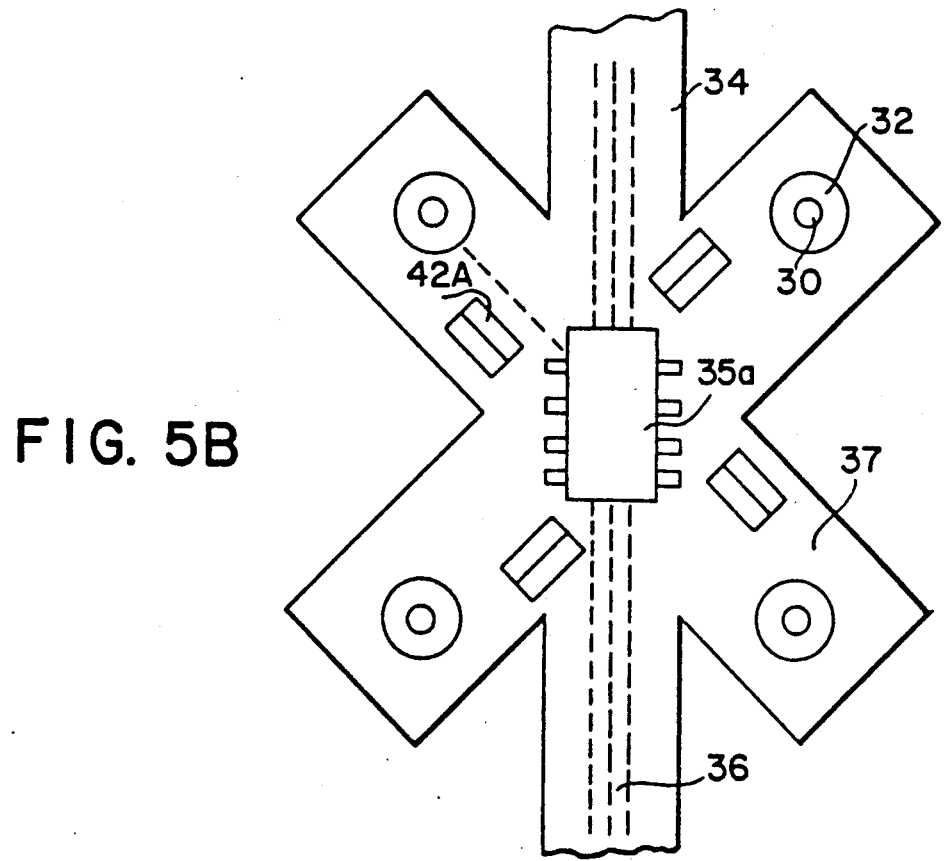
FIG. 5B is an enlarged view of a portion of FIG. 5A

As shown in FIGS. 4 and 5, a gold-plated pin 30 from each of the electrodes 12a-n plugs into a contact spring receptacle 31 having a pair of gold-plated spring contacts 32. The receptacle is attached to a metal pad (with a plated-through hole) on the flexible non-conductive printed circuit board 34. Conductors 36, which are copper foil signal traces, conduct the signals from each electrode 12a-n to a nearby preamplifier circuit 35a. The flexible printed circuit board 34 is preferably composed of a polyamide material having a copper foil ground plane 37 on the top side and signal trace conductors 36 on the bottom side. The ground plane 37 serves to shield the signal traces and electrodes from pickup of stray noise. The hat 10 employs 1 to 64 quad FET input amplifier integrated circuits 35a-n such as the Burr Brown OPA404KP, for low-noise preamplification of the microvolt EEG signals by a factor of 100 to a 10 mV range. Each preamplifier 35a-n services four electrodes. Two resistors 42 determine the gain of the preamplifier circuit. Each integrated preamplifier circuit 35a-n is connected by solder 40 to the flexible printed circuit board 34 using an amplifier input lead 38 and a pad 39 with plated-through hole.

As shown in FIGS. 3A-3D and 4, each of the electrodes 12a-n includes a plurality of flexible fingers 17.

The embodiment of FIG. 3A has six flexible fingers 17; the embodiment of FIG. 3B has three flexible fingers 17 (2.0 cm in diameter); the embodiment of FIG. 3C is a blow up of the dimpled free end 18 of a single flexible finger 17; the embodiment of FIG. 3D is a top plan view of the electrode of the embodiment of FIG. 3A as a flat sheet prior to being formed into an electrode. As shown in FIG. 4, each of the electrodes 12a-n has a plurality of flexible metal fingers 17 terminating at the free end in a dimpled tip 18. A conductive metal solder 20 attaches the electrode 12a-n to the bottom of the gold-plated pin 30. The dimpled tips 18 contact the scalp 21.

As shown in FIG. 5, the flexible printed circuit board 34 conducts signals from the outputs of the preamplifier circuits 35a-n (circuits 35a-d being shown in FIG. 5) to a common point at the back of the head where a connector 41 to a standard cable (42 shown in FIG. 1) conducts the signals off the head. Power for the preamplifiers is preferably provided by a battery pack 15 located at the back of the head and consists of 2 batteries such as Electrochem Industries 3B50. Ear clip reference electrode 13a plugs in to extensions 13b to the printed circuit board 34. An amplifier circuit 43, located at the back of the head, amplifies and adds together the signals from the reference electrodes.

Figure 6:
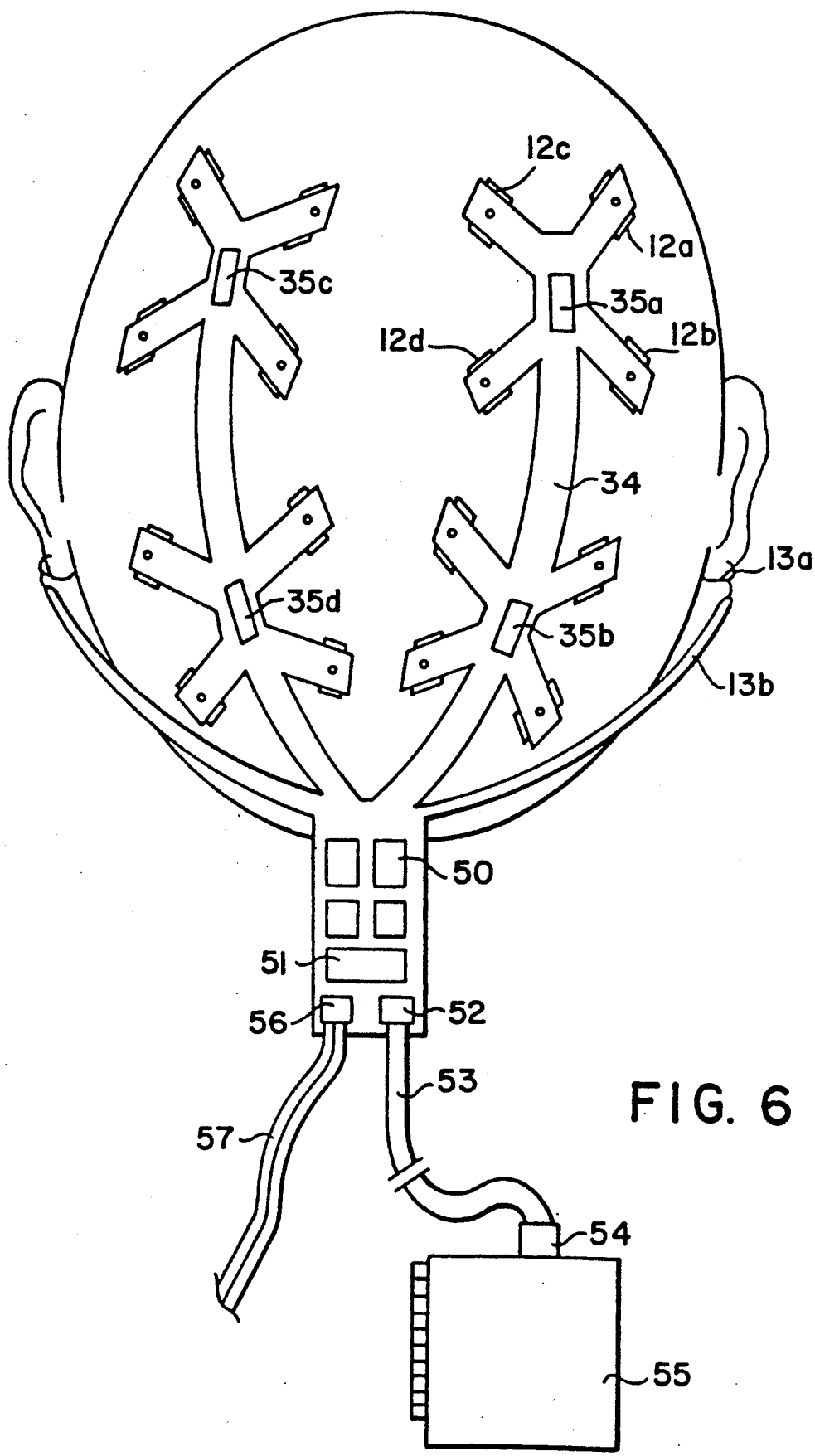
FIG. 6 is a top view of the digital embodiment of the hat with cover removed, to show the encoder chips, digital multiplexing circuitry, fiber optic transmitter, and decoder circuit board.

An additional embodiment of the battery pack 15, consists of a small container (not shown) with 4 Alkaline D cells which are connected to connector 56, FIG. 6, by cable 57. The battery pack (not shown) can be worn across the shoulder or in a pocket.

In order to allow the stretchable cap to adapt to the head shape of each patient, slack is allowed in the printed circuit board between each arm of each four-electrode cluster, as well as between clusters and the collection point at the back of the head. The printed circuit board is attached to the hat 11 with Velcro (TM). The cloth hat cover 14 attaches to the stretchable hat body 11 with a Velcro (TM) rim 16. For cleaning, each electrode is unplugged from the printed circuit board, and the stretchable cap and electrodes are separated as a unit from the printed circuit board 34 and hat cover 14.

As shown in FIG. 6, the digital embodiment of the Smart Hat has several components in addition to those of the analog embodiment described above. In the digital embodiment of FIG. 6, (1) From 1 to 16 encoder circuits 50 each perform filtering, amplification, digitization, and multiplexing of the outputs from the preamplifier circuits. Each encoder circuit services 16 channels;

(2) A digital multiplexing circuit 51 multiplexes the outputs of the encoder circuits;

(3) A fiber optic transmitter 52 translates the output of the digital multiplexing circuit to a stream of light pulses;

(4) A fiber optic cable 53, fiber optic receiver 54 and decoder circuit 55 to translate from light to digital form, demultiplex the signal and convert the signal into a sequence of parallel binary words readable by a computer.

Three alternate embodiments of communication media may be used in place of the fiber optic system (as shown in FIG. 6); fiber optic transmitter 52, fiber optic cable 53 and fiber optic receiver 54. These embodiments are: 1) Coaxial cable, 2) Radio link or 3) Infra-red link.

Figure 10A:
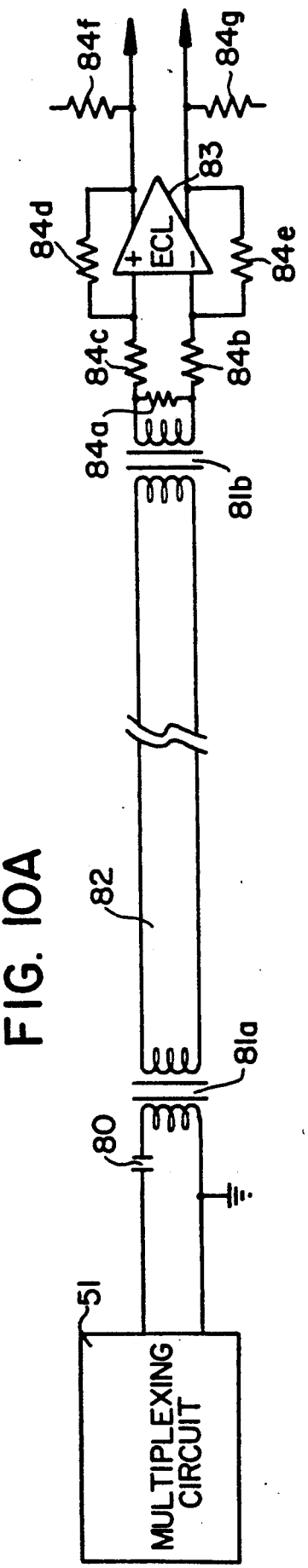
FIG. 10A is a preferred embodiment of a coaxial cable transmission link.

A preferred embodiment of the coaxial cable link is illustrated in FIG. 10A. The digital output from multiplexing circuit 51 is differentiated by the capacitor 80, which typically might range between 20 and 100 picofarads. This a.c. signal is passed through a Radio Frequency (RF) transformer 81a, such as Mini Circuits T1-6T, which serves to isolate the sensitive circuitry on the hat from the noisy signals in the demultiplexing circuit on the decoder board 55 (not shown) and in the computer interface. The resulting signal is sent over a standard RF coaxial cable 82, such as type RG-174 cable, made by many manufacturers. A second RF transformer 81b at the end of the coaxial cable 82 converts the single ended signal into a differential signal to be fed into the differential ECL line receiver 83. The resistor 84a serves to properly terminate the signals from the cable 82, so as to prevent signal reflections. Resistors 84b-g provide hysteresis to the ECL line receiver 83, enabling the outputs to remain in the stable state specified by the input pulse stream. In this way, a positive-going pulse causes the output to go to, and remain in, a high state, and a negative-going pulse will make the output go to, and remain in, a low state.

FIG. 10B illustrates a further embodiment of the coaxial cable link, shown previously in FIG. 10A. In the extended version the coaxial cable 82 is used to supply isolated power to the hat electronics in addition to transferring isolated EEG data to the decoder electronics 55 (FIG. 6). Operation is very similar to that of FIG. 10A, except that an isolated power supply (located on the board with the decoder electronics 55) superimposes a d.c. voltage on top of the incoming a.c.-coupled EEG data waveform. This d.c. voltage is generated with a conventional switching inverter composed of transistors 85a and 85b and isolation transformer 86. Transistors 85a and 85b commutate at 250 KHz or more. The reason for using such a high frequency, is that this allows the power transformer 86 to be very small, minimizing parasitic capacitance between primary and secondary, and thereby minimizing coupling of noise from the decoder board 55 to the coaxial cable 82 carrying power to the hat.

The d.c. voltage, which is simply obtained by rectifying the voltage at the secondary of the power transformer 86, is fed via the low pass filter comprised of inductors 87a-d and capacitors 88a-b onto the coaxial cable 82. Inductors 87c and 87d are particularly important, as they prevent the incoming high-frequency data pulses from being attenuated by the impedance of the power supply (which is connected in parallel with the coaxial cable 82).

On the hat end of the coaxial cable 82, the d.c. power is picked up through the low-pass filter (inductor 87e and capacitor 88c) and is used to power the entire hat electronics, thereby eliminating the need for batteries while providing a safe, isolated power source for the hat.

A preferred embodiment of the Radio link is illustrated in FIG. 11. In this embodiment, a standard FM transmitter 90a and receiver 91a, of conventional design, are used. When the multiplexing circuit 51 outputs a digital "0" the FM transmitter's voltage-controlled oscillator (VCO) 90b generates a high RF frequency near 450 MHz. On the other hand, a digital "1" from the multiplexing circuit 51 would cause the VCO 90b to generate a slightly lower frequency, say 440 MHz. The RF signals are amplified by a conventional RF amplifier 90c and sent to a small antenna 90d.

The RF signal propagates through the room and is received by a second antenna 91c, connected to a conventional FM receiving circuit 91b, which produces an output voltage proportional to the frequency of the incoming radio frequency. The receiver 91a is tuned so that it produces a negative voltage when the incoming frequency is higher than 445 MHz, and a positive voltage when the incoming frequency is lower that 445 MHz. In this way the comparator 91d (such as National Semiconductor LM311) will produce a logic 0 when a frequency of 450 MHz is seen, and a logic 1 when a frequency of 440 MHz is seen.

Figure 12:
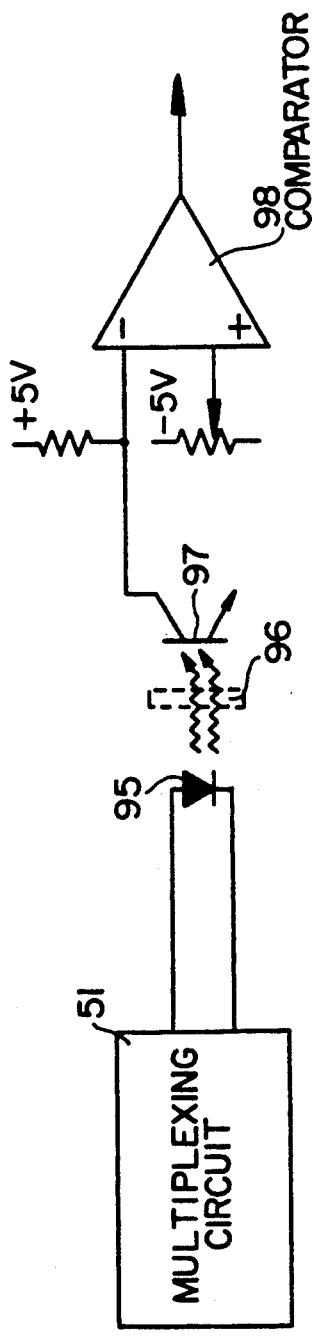
FIG. 12 is a preferred embodiment of an infra-red (IR) transmission link.

A preferred embodiment of an infra-red communication link is illustrated in FIG. 12. A logic "1" from multiplexing circuit 51 causes the infra-red (IR) light emitting diode (LED) 95 to light up. An IR transmission filter (96) on the receiving end blocks out all light except for a narrow band at the wavelength of the IR LED 95. IR phototransistor 97 conducts more heavily, producing a voltage which is modified by the comparator 98, with the resulting "recovered bit stream" sent to the demultiplexing circuitry 55 (not shown).

As shown in FIG. 6, the encoding circuits are preferably mounted on the hat which requires that electronics for each group of 16 channels be implemented with a custom integrated circuit for simplicity and small physical size. If active circuitry is placed off the hat, commercially available IC's may be used. The decoder circuit 55 is contained on a printed circuit board which resides in the data analysis computer.

Figure 7:
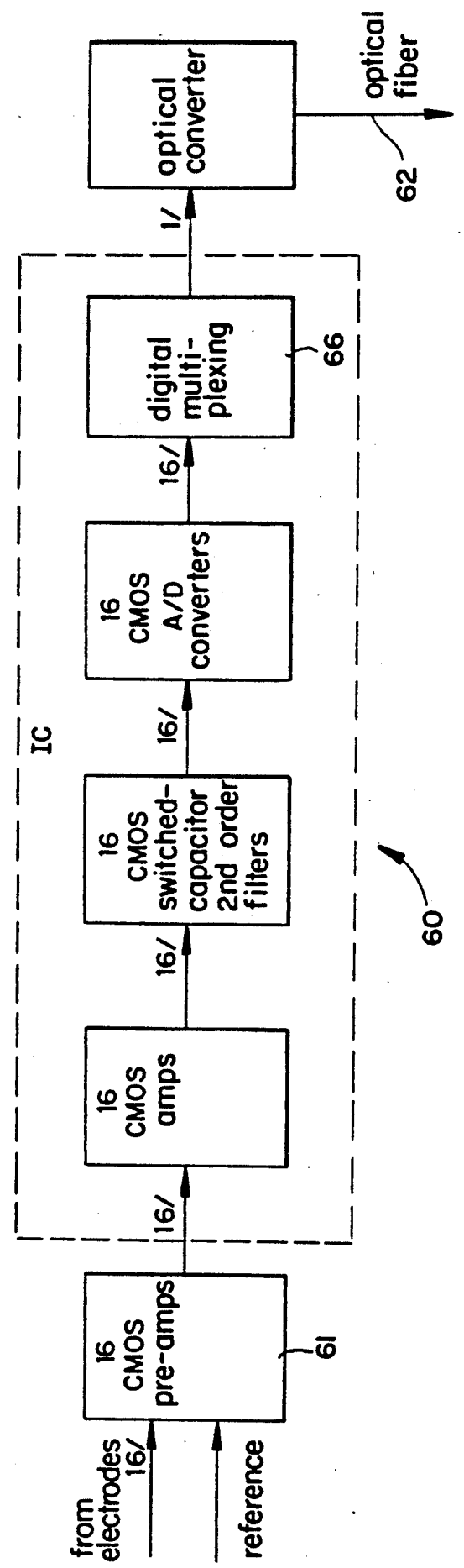
FIG. 7 is a block diagram of the encoder circuit.

As shown in FIG. 7, the preferred IC implementation of the encoder circuit employs a delta-sigma A/D on each chip, resulting in a high-rate (512 Kbit/sec) one-bit digital output from each chip. The essence of the electronics design is a semi-custom LSI integrated circuit 60 which converts preamplified EEG voltages from 16 channels, i.e., from CMOS preamps 61, to an oversampled bit stream using switched-capacitor filters and sigma-delta converters. The voltages are picked up at the scalp using the aforementioned flexible metal alloy, multicontact electrodes 12a-n, pre-amplified using the aforementioned commercial FET input amplifiers 35a-n, and then amplified, filtered and converted using a circuit 60 which is preferably implemented in a semi-custom IC based on standard commercially available IC building blocks. In a preferred embodiment, an optical fiber is used to carry the final multiplexed signal from the hat to a decoder circuit located nearby.

The IC 60 performs amplification by a factor of about 100, antialiasing filtering provided by the combination of a fixed RC pole at 128 Hz and a variable 2nd-order switched-capacitor biquad filter, sigma-delta conversion to an oversampled bit stream at a rate 64 times the Nyquist rate (16384 Hz for 128 Hz bandwidth data), and multiplexing to a signle 1-bit channel. The sampling rate and corresponding filter cutoff is proportional to the frequency of the clock signal supplied to the switched capacitor filters. The latter will be variable from 32 to 128 Hz. The six octave oversampling means that the two-pole filter attenuates by roughly 72 dB at half the sampling frequency. The gain and filtering is accomplished by a single switched-capacitor filter circuit which uses two standard parasitic-insensitive switched-capacitor integrators. The sigma-delta circuit also uses two switched-capacitor integrators, but also requires a simple comparator to do the single-bit digitization. The outputs of sixteen channels are multiplexed (digital multiplexing 66) with a standard digital circuit design. All circuits are designed and fabricated in a CMOS process, which makes good capacitors, switches, and integrating amplifiers, and can be easily designed for low power consumption.

Figure 8:
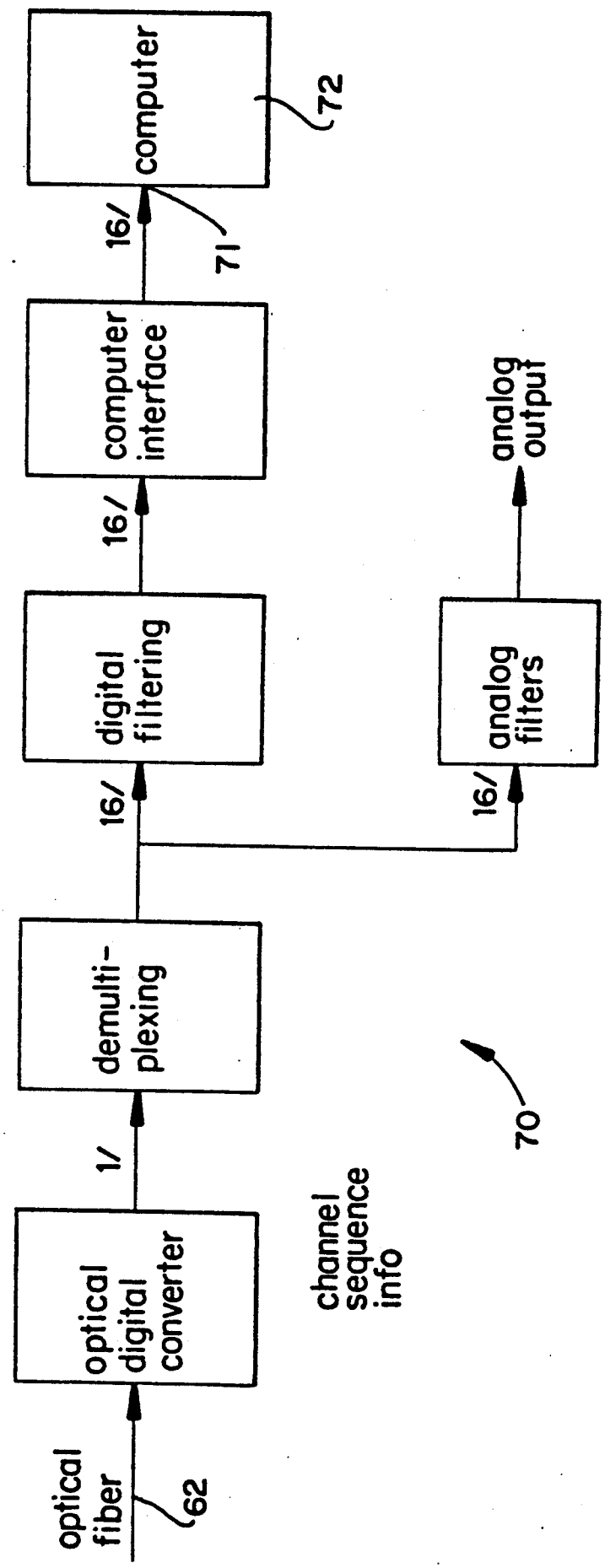
FIG. 8 is a block diagram of the sigma-delta decoder.

As shown in FIG. 8, the decoder circuit 70 demultiplexes the high-rate bit stream from the optical fiber 62 into 12-bit, or optionally 16-bit, representations of each of the signal channels, and makes the data available to a parallel input port 71 of a computer 72.

Each of the sixteen amplification/filtering/quantization modules on the chip 60 is a complete unit with connections only at the input and output. Gain, filtering and digitization sections have no interconnections between channels. This greatly simplifies IC design and layout, interconnect is essentially only within the area allotted for each channel. Each channel is essentially an independent module which can be separately characterized and simulated. This simplicity also implies that a single level of metallization should be quite sufficient for the design, which permits use of well-proven CMOS IC processes. A post-processing circuit translates multiplexed digital signals into two's complement 12-bit, or optionally 16-bit, binary form, which are stored on a computer.

Figure 9:
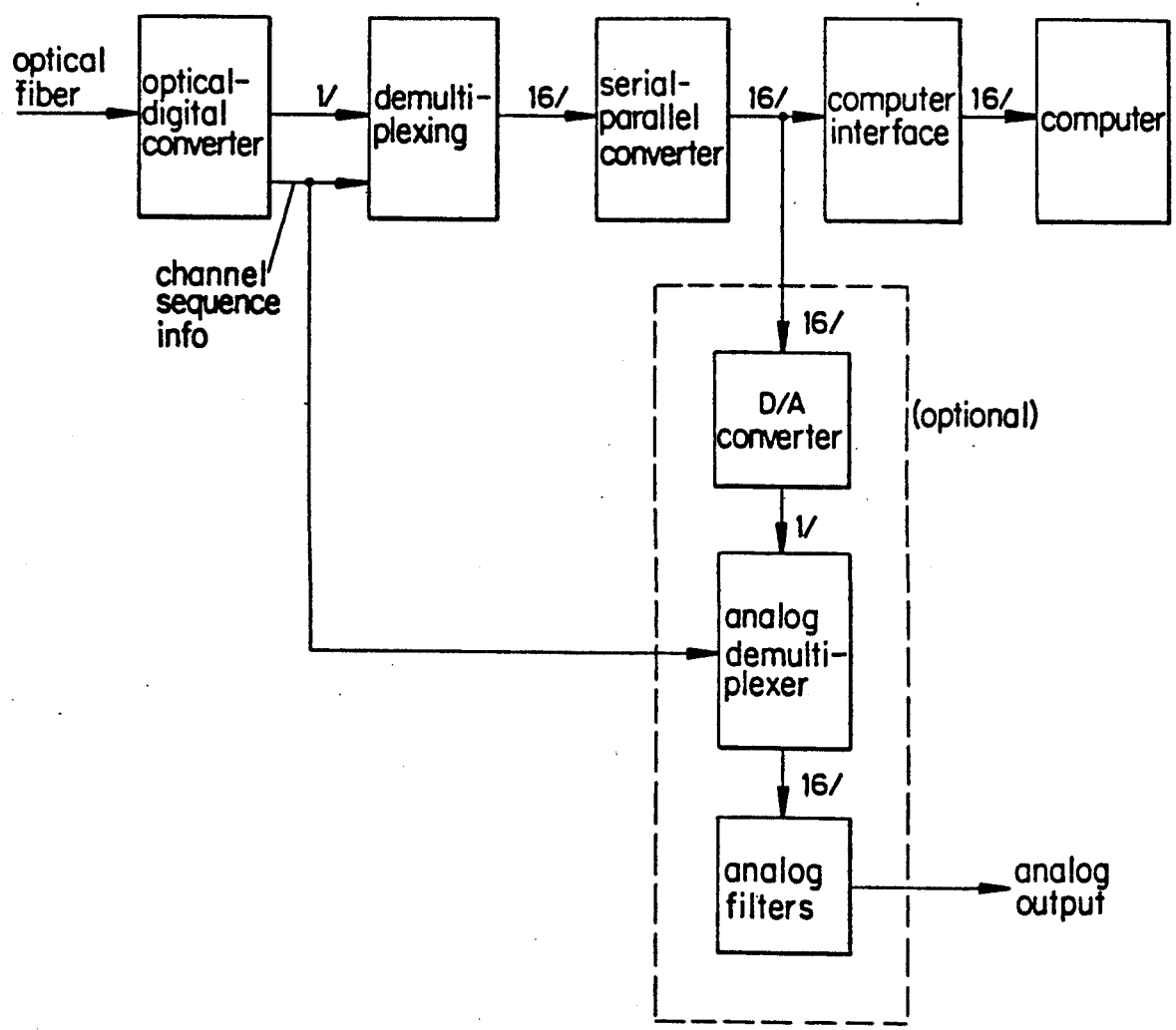
FIG. 9 is a block diagram of the offset binary decoder.

An alternative embodiment of the digitally multiplexed hat uses 16 12-bit, or optionally 16-bit, integrating A/D converters (as opposed to delta-sigma converters) to generate full offset binary directly. FIG. 9 shows the decoder circuit for this alternative embodiment. This requires one additional 12-bit, or optionaly 16-bit, counter per channel on the IC, and necessitates digital to analog (D/A circuitry in the decoder circuit to retrieve the analog signal). In applications requiring digital output only, the availability of low-bit-rate binary code without additional digital filtering is advantageous. The demultiplexing can also be at a lower rate in this instance.

Although the above-described embodiments relate to a stretchable fabric hat, the multifinger flexible metal alloy electrodes of the present invention may be mounted within a stiff plastic helmet ("Smart Helmet"), for example, a pilot's flight helmet. The electrodes are mounted on a soft liner mounted in the helmet, and the signals conducted to the preamplifier and amplifier circuits attached in the helmet by snaps or other fasteners. The metal alloy of the electrodes 12a-n may be made of Beryllium Copper or other suitable alloys, providing the required compliance. In an additional embodiment, the helmet electrodes are preferably constructed of 1-inch diameter foam disks covered with conductive silver cloth (not shown). The electrodes connect with the printed circuit board in a manner consistent with the flexible metal finger electrodes.

In a separate embodiment, a reduced number of biophysical input channels and accompanying electronics would be mounted onto a stretchable headband or pair of padded goggles (not shown), to record eye movements and/or EEG's. These signals could then be used to influence or control devices such as computer/video games, or bio-feedback systems.

We claim:

1. An electrode system to detect brain waves from the scalp of a patient, the system comprising:
   a head gear adapted to fit on the head of the patient;
   at least one electrode mounted on the head gear to contact the scalp, said at least one electrode comprising a plurality of stiff conductive fingers each having a free end portion, a tip means at the end of each finger free end portion to contact the scalp of the patient without abrading or hurting the scalp, said tip means including a conductive tip to contact the scalp, said tip having a diameter of greater than 0.1-inch at its contact with the scalp and a surface which is smooth, non-pointed and non-abrasive to the scalp, and conductive means including said fingers to conduct brain wave signals from the tips.

2. An electrode system as in claim 1 wherein each tip has a cup-like indentation whose open end is directed toward the scalp.

3. An electrode system as in claim 1 wherein the head gear is a flexible hat and further including a flexible circuit board means within and conforming to the hat to conduct the brain wave signals and amplifier means mounted on said circuit board means to amplify the brain wave signals.

4. An electrode system as in claim 1 wherein each of said fingers has a conductive metal shank portion and a conductive metal tip portion extending from said shank portion generally perpendicular thereto.

5. An electrode system as in claim 3 wherein said circuit board means includes an insulative circuit board, a conductive ground plane foil adhered on one side thereof and signal trace elongated foil conductors adhered to the opposite side thereof.

6. An electrode system as in claim 3 wherein the amplifier means includes at least one input low-noise preamplifier having FET inputs.

7. An electrode system as in claim 3 wherein the hat has a plurality of electrodes and said amplifier means comprises at least one integrated circuit quad amplifier.

8. An electrode system as in claim 3 and further including an encoder circuit mounted on said circuit means, a digital multiplexing circuit mounted on said circuit board means, a fiber optic transmitter mounted on said circuit board means and an optic fiber cable connected to said optic transmitter;
   wherein said brain waves are converted to digital data, multiplexed, converted to optical signals and transmitted on said optical fiber cable.

9. An electrode system as in claim 3 and further including, mounted on said circuit board means, an integrated circuit including a plurality of input channels and connected to each channel a multi-bit analog-to-digital converter.

10. An electrode system as in claim 1 wherein said head gear is a flexible elastic hat.

11. An electrode system as in claim 1 wherein said head gear is an elastic band.

12. An electrode system as in claim 1 wherein said head gear is a helmet.

* * * * *